United States Patent [19]

Tanaka et al.

[11] Patent Number: 5,283,341

[45] Date of Patent: Feb. 1, 1994

[54] N-ALKYLATION OF HETEROCYCLIC, AROMATIC AMINES

[75] Inventors: Norio Tanaka; Masataka Hatanaka, both of Funabashi; Yoshihisa Watanabe, Jyoyo, all of Japan

[73] Assignee: Nissan Chemical Industries Ltd., Tokyo, Japan

[21] Appl. No.: 880,587

[22] Filed: May 8, 1992

[30] Foreign Application Priority Data

May 9, 1991 [JP] Japan .................................. 3-104388
Mar. 27, 1992 [JP] Japan .................................. 4-070802

[51] Int. Cl.$^5$ .................... B01J 23/46; C07D 233/54; C07D 249/22; C07D 403/02
[52] U.S. Cl. .................... 548/262.2; 548/110; 548/304.4; 548/355.1; 548/300.1; 548/373.1; 548/374.1; 548/579; 564/480; 502/155; 502/162; 502/326
[58] Field of Search .................... 548/335, 579, 356.1, 548/373.1, 374.1, 335.1, 304.4, 262.2, 110; 564/480

[56] References Cited

U.S. PATENT DOCUMENTS

| | | | |
|---|---|---|---|
| 3,223,734 | 12/1965 | Fallstad et al. | 564/480 |
| 3,600,413 | 8/1971 | Grimm | 564/480 X |
| 3,708,539 | 1/1973 | Fenton et al. | 564/480 |
| 4,105,657 | 8/1978 | Dockner et al. | 548/300.1 |

FOREIGN PATENT DOCUMENTS

| | | |
|---|---|---|
| 0034480 | 8/1981 | European Pat. Off. . |
| 0147188 | 7/1985 | European Pat. Off. . |
| 2342728 | 9/1977 | France . |

OTHER PUBLICATIONS

Patent Abstracts of Japan, vol. 2, No. 52, Apr. 14, 1978, & JP-A-53-009-725, Jan. 28, 1978, H. Hayamizu, et al., "Preparation of N-Alkylaromatic Amines".
Bulletin of the Chemical Society of Japan, vol. 50, No. 6, pp. 1510–1512, Jun. 1977, M. Hayashi, et al., "N-Alkylation Of Nitrogen Heterocyclic Compounds With Dialkyl Phosphites".
Journal of the American Chemical Society, vol. 101, No. 1, pp. 490–491, Jan. 17, 1979, S. E. Diamond, et al., "Reactions Of Aniline With Olefins Catalyzed by Group 8 Metal Complexes: N-Alkylation And Heterocycle Formation".

Primary Examiner—Floyd D. Higel
Attorney, Agent, or Firm—Oblon, Spivak, McClelland, Maier & Neustadt

[57] ABSTRACT

A process for producing a heterocyclic tertiary amine of the formula (III):

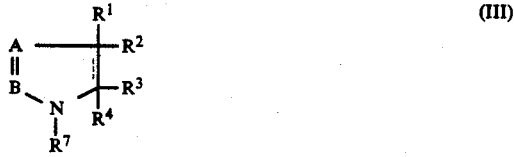

wherein A is a nitrogen atom or C-$R^5$, B is a nitrogen atom or C-$R^6$, ==== is a single bond or a double bond, and each of $R^1$, $R^2$, $R^3$, $R^4$, $R^5$ and $R^6$ which may be the same or different, is a hydrogen atom, an acyl group, a halogen atom, a cyano group, etc., provided that two of $R^1$, $R^2$, $R^3$ and $R^4$ may together form a 3-membered, 4-membered, 5-membered or 6-membered aliphatic ring, a heterocyclic rig or aromatic ring, and $R^7$ is a $C_{1-6}$ alkyl group which may be substituted, etc., which process comprises reacting a heterocyclic secondary amine of the formula (I):

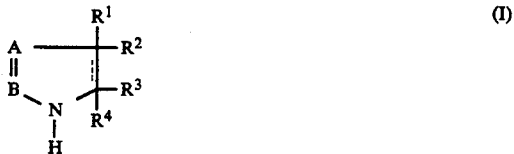

wherein A, B, ==, $R^1$, $R^2$, $R^3$ and $R^4$ are as defined above, with an alkylating agent of the formula (II):

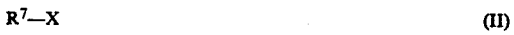

$$R^7-X \qquad (II)$$

wherein $R^7$ is as defined above, and X is a hydroxyl group, a halogen atom, a $OSO_3R^7$ group, a $OSO_2R^7$ group, a $OCO_2R^7$ group, a $OCOR^7$ group, a $OP(O)(OR^7)$ group, a $OP(O)O(R^7)_2$ group or an amino group, in the presence of a catalyst of Group VIII of the Periodic Table.

8 Claims, No Drawings

N-ALKYLATION OF HETEROCYCLIC, AROMATIC AMINES

The present invention relates to a process for producing a heterocyclic tertiary amine, which comprises N-alkylating a heterocyclic secondary amine in the presence of a catalyst of Group VIII of the Periodic Table. The heterocyclic tertiary amines are a group of compounds useful as intermediates for various fine chemicals including physiologically active substances such as pharmaceuticals and agricultural chemicals.

Heretofore, as a common method for producing a heterocyclic tertiary amine, a method is known wherein a cyclic secondary amine is reacted with an active alkylating agent represented by an alkyl halide or a dialkyl sulfate, in the presence of a base.

As the most basic methylation reaction by means of methyl halide or dimethyl sulfate, N-methylation of a pyrrole is reported in Angew. Chem. Int. Ed. Engl., vol. 27, No. 19, p. 1170 (1988).

N-methylation of an imidazole ring is reported in J. Org. Chem., vol. 49, No. 16, p. 2887 (1984).

N-methylation of a pyrazole ring is reported in e.g. J. Org. Chem. vol. 49, No. 24, p. 4687 (1984), or J. Med. Chem., vol. 27, No. 4, p. 539 (1984).

N-methylation of an indole ring is reported in Org. Synth. Coll. Vol., vol. 5, p. 769 (1973).

N-methylation of a benzimidazole ring is reported in e.g. Synthesis, p. 124 (1981), or Ann. Chem., p. 1078 (1983).

N-methylation of a pyrazoline ring is reported in Bull. Chem. Soc. Jpn., vol. 56, p. 918 (1983).

N-methylation of a purine ring is reported in e.g. Chem. Ber., vol. 82, p. 201 (1950).

Further, N-alkylation reactions have been reported in which benzyl alcohol derivatives (Chem. Ind., p. 85 (1980)), carboxylic acid esters (Synthesis, p. 382 (1986)), phosphoric acid esters (Bull. Chem. Soc. Jpn., vol. 50, p. 1510 (1977)), amidoacetal (J. Org. Chem., vol 49, No. 9, p. 1549 (1984)), sulfur ylide (J. Org. Chem. vol. 35, p. 3918 (1970)) or Meerwein reagents (Chem. Ber., vol. 118, No. 8, p. 3424 (1985)) are used as alkylating agents.

Such conventional methods require relatively expensive alkylating agents, and in many cases, at least equivalent of a base or a condensation agent is required, and problematic by-products such as salts are often produced. Further, in some cases, the reactions tend to be affected by moisture, whereby due care is required for the operation.

Accordingly, it has been desired to develop a method for producing a heterocyclic tertiary amine, which is applicable to heterocyclic secondary amines having various substituents as starting materials and which can be safely and inexpensively conducted on an industrial scale.

The present inventors have conducted extensive studies to solve the above problems and a result, have succeeded in accomplishing the present invention.

The present invention provides a process for producing a heterocyclic tertiary amine of the formula (III):

wherein A is a nitrogen atom or C-$R^5$, B is a nitrogen atom or C-$R^6$, ==== is a single bond or a double bond, and each of $R^1$, $R^2$, $R^3$, $R^4$, $R^5$ and $R^6$ which may be the same or different, is a hydrogen atom, an acyl group, a halogen atom, a cyano group, a nitro group, a carboxyl group, a formyl group, a trialkylsilyl group, a $C_{1-6}$ alkoxycarbonyl group which may be substituted (the substituent being a hydroxyl group, a halogen atom, a cyano group, a nitro group, a carboxyl group, a formyl group a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a phenyl group, a phenoxy group or a phenylthio group), a $C_{1-6}$ alkylcarbonyloxy group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl. group, a phenyl group, a phenoxy group or a phenylthio group), a $C_{1-6}$ alkoxy group which may be substituted (the substituent being a hydroxyl group, a halogen atom, a cyano group, a nitro group, a carboxyl group, a formyl group, a lower alkoxy group, a lower alkylthio group, a lower alkoxy carbonyl group, an acyl group, a benzoyl group, a di-lower alkylamino group, a lower alkylsulfenyl group, a lower alkylsulfonyl group, a phenyl group, a phenoxy group or a phenylthio group), a $C_{1-6}$ dialkylamino group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a phenyl group, a phenoxy group or a phenylthio group), a $C_{1-6}$ alkylthio group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a phenyl group, a phenoxy group or a phenylthio group), a $C_{1-6}$ alkylsulfenyl group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, di-lower alkylamino group, a lower alkylsulfenyl group, a lower alkylsulfonyl group, a phenyl group, a phenoxy group or a phenylthio group), a $C_{1-6}$ alkylsulfonyl group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a phenyl group, a phenoxy group or a phenylthio group), a $C_{1-6}$ alkylsulfonyloxy group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a phenyl group, a phenoxy group or a phenylthio group), a $C_{1-6}$ alkyl group which may be substituted (the substituent being a hydroxyl group, a halo9en atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a phenyl group, a phenoxy group or a phenylthio group), a $C_{2-6}$ alkenyl group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a phenyl group, a phenoxy group or a phenylthio group), a $C_{2-6}$ alkynyl group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulphenyl group, a lower alkylsulphonyl group, a phenyl group, a phenoxy group or a phenylthio group), or a phenyl group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a phenyl group, a phenoxy group or a phenylthio group), provided that two of $R^1$, $R^2$, $R^3$ and $R^4$ may together form a 3-membered, 4-membered, 5-membered or 6-membered aliphatic ring, heterocyclic ring or aromatic ring, and provided that $R^2$ and $R^4$ may together form a bond so that ---- is a double bond, and $R^7$ is a $C_{1-6}$ alkyl group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di lower alkylamino group, a lower alkylsulfenyl group, a lower alkylsulfonyl group, a trialkylsilyl group, a phenyl group, a phenoxy group or a phenylthio group), a $C_{2-6}$ alkenyl group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a trialkylsilyl group, a phenyl group, a phenoxy group or a phenylthio group), a $C_2-6$ alkynyl group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a trialkylsilyl group, a phenyl group, a phenoxy group or a phenylthio group), or a phenyl group which may be substituted (the substituent being a hydroxyl group, a halogen atom, a cyano group,.a nitro group, a carboxyl group, a formyl group, a lower alkoxy group, a lower alkylthio group, a lower alkoxy carbonyl group, an acyl group, a benzoyl group, a di-lower alkylamino group, a lower alkylsulfenyl group, a lower alkylsulfonyl group, a trialkylsilyl group, a phenyl group, a phenoxy group or a phenylthio group), which process comprises reacting a heterocyclic secondary amine of the formula (I):

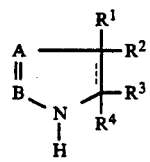

(I)

wherein A, B, ----, $R^1$, $R^2$, $R^3$ and $R^4$ are as defined above, with an alkylating agent of the formula (II):

$$R^7-X \qquad (II)$$

wherein $R^7$ is as defined above, and X is a hydroxyl group, a halogen atom, a $OSO_3R^7$ group, a $OSO_2R^7$ group, a $OCO_2R^7$ group, a $OCOR^7$ group, a $OP(O)(OR^7)$ group, a $OP(O)O(R^7)_2$ group or an amino group, in the presence of a catalyst of Group VIII of the Periodic Table.

Now, the present invention will be described in detail with reference to the preferred embodiments.

With respect to $R^1$, $R^2$, $R^3$, $R^4$, $R^5$ and $R^6$ in the above formulas, the acyl group includes, for example, an acetyl group, a propanoyl group, a butanoyl group, an allylcarbonyl group, a propargylcarbonyl group, a cyclopropylcarbonyl group, a hexanoyl group, a cyclohexylcarbonyl group, a benzoyl group, a toluoyl group and a benzylcarbonyl group.

The halogen atom includes, for example, a fluorine atom, a chlorine atom, a bromine atom and an iodine atom.

The trialkylsilyl group includes, for example, a trimethylsilyl group and a triethylsilyl group.

The $C_{1-6}$ alkoxycarbonyl group which may be Substituted, includes, for example, a methoxycarbonyl group, an ethoxycarbonyl group, a n-propoxycarbonyl group, an i-propoxycarbonyl group, a trifluorimethoxycarbonyl group, a cyanoethoxycarbonyl group, a nitromethoxycarbonyl group, a methoxyethoxycarbonyl group, a methylthiomethyloxycarbonyl group, a methoxycarbonylmethoxycarbonyl group, an acetylmethoxycarbonyl group, a benzoyloxycarbonyl group, a dimethylaminoethyloxycarbonyl group, a methanesulfoxyethoxycarbonyl group, a methanesulfonylmethoxycarbonyl group, a phenoxycarbonyl group, a phenoxyethoxycarbonyl group and a phenylthioethoxycarbonyl group.

The $C_{1-6}$ alkylcarbonyloxy group which may be substituted, includes, for example, an acetyloxy group, a propanoyloxy group, a butanoyloxy group, an allylcarbonyloxy group, a propargylcarbonyloxy group, a cyclopropylcarbonyloxy group, a hexanoyloxy group, a cyclohexylcarbonyloxy group, a benzoyloxy group, a toluoyloxy group, a benzylcarbonyloxy group, a trifluorocarbonyloxy group, a cyanoethoxycarbonyloxy group, a nitromethoxycarbonyloxy group, a methoxyethoxycarbonyloxy group, a methylthiomethyloxycarbonyloxy group, a methoxycarbonylmethoxycarbonyloxy group, an acetylmethoxycarbonyloxy group, a benzoyloxycarbonyloxy group, a dimethylaminoethyloxycarbonyloxy group, a methanesulfoxyethoxycarbonyloxy group, a methanesulfonylmethoxycarbonyloxy group, a phenoxymethylcarbonyloxy group, a phenoxyethoxycarbonyloxy group and a phenylthioethoxycarbonyloxy group.

The $C_{1-6}$ alkoxy group which may be substituted, includes, for example, a methoxy group, an ethoxy group, a propoxy group, a butoxy group, an amyloxy group, a hexyloxy group, a trifluoromethoxy group, a difluoromethoxy group, a hydroxyethoxy group, a cyanoethoxy group, a nitroethoxy group a methoxymethoxy group, a methoxyethoxy group, an ethoxymethoxy group, a methylthiomethoxy group, an ethylthiomethoxy group, a methoxycarbonylmethoxy group, a benzoylmethoxy group, a dimethylaminomethoxy group, a methyl sulfinylmethoxy group, a methanesulfonylmethoxy group, a benzyloxy group, a phenoxyethoxy group and a phenylthioethoxy group.

The $C_{1-6}$ dialkylamino group which may be substituted, includes, for example, an N,N-dimethylamino group, an N,N-diethylamino group, an N-methyl-N-methoxy group, an N-methyl-N-methoxycarbonylmethylamino group, an N-methyl-N-phenylamino group, an N-methyl-N-acylamino group, an N-methyl-N-benzoylamino group and an N-methyl-N-methanesulfonylamino group.

The $C_{1-6}$ alkylthio group which may be substituted, includes, for example, a methylthio group, an ethylthio group, a propylthio group, butylthio group, an amylthio group, a hexylthio group, a trifluoromethylthio group, a difluoromethylthio group, a cyanoethylthio group, a nitroethylthio group, a methoxymethylthio group, a methoxyethylthio group, an ethoxymethylthio group, a methylthiomethylthio group, an ethylthiomethylthio group, a methoxycarbonylmethylthio group, a benzoylmethylthio group, a dimethylaminomethylthio group, a methylsulfinylmethylthio group, a methanesulfonylmethylthio group, a benzylthio group, a phenoxyethylthio group and a phenylthioethylthio group.

The $C_{1-6}$ alkylsulfenyl group which may be substituted, includes, for example, a methylsulpfenyl group, an ethylsulfenyl group, a propylsulfenyl group, a butylsulfenyl group, an amylsulfenyl group, a hexylsulfenyl group, a trifluoromethylethylsulfenyl group, a methoxymethylsulfenyl group, a methoxyethylsulfenyl group, an ethoxymethylsulfenyl group, a methoxycarbonylmethylsulfenyl group, a benzoylmethylsulfenyl group and a phenoxyethylsulfenyl group.

The $C_{1-6}$ alkylsulfonyl group which may be substituted, includes, for example, a methanesulfonyl group, an ethanesulfonyl group, a propylsulfonyl group, butylsulfonyl group, an aminosulfonyl group, a hexylsulfonyl group, a trifluoromethylethylsulfonyl group, a cyanoethylsulfonyl group, a nitroethylsulfonyl group, a methoxymethylsulfonyl group, a methoxymethylsulfonyl group, a methoxyethylsulfonyl group, an ethoxymethylsulfonyl group, a methoxycarbonylmethylsulfonyl group, a dimethylaminomethylsulfonyl group, a methanesulfonylmethylsulfonyl group, a benzylsulfonyl group and a phenoxyethylsulfonyl group.

The $C_{1-6}$ alkylsulfonyloxy group which may be substituted, includes, for example, a methanesulfonyloxy group, an ethanesulfonyloxy group, a propylsulfonyloxy group, a butylsulfonyloxy group, an amylsulfonyloxy group, a hexylsulfonyloxy group, a trifluoromethylsulfonyloxy group, a cyanoethylsulfonyloxy group, a benzenesulfonyloxy group and a toluenesulfonyloxy group.

The $C_{1-6}$ alkyl group which may be substituted, includes, for example, a methyl group, an ethyl group, a propyl group, a butyl group, an amyl group, a hexyl group, a trifluoromethyl group, a cyanomethyl group, a nitromethyl group, a methoxycarbonylmethyl group, an ethoxycarbonylmethyl group, a hydroxycarbonylmethyl group, a hydroxymethyl group, a formylmethyl group, a methoxymethyl group, an ethoxymethyl group, a methylthiomethyl group, an ethylthiomethyl group, an acetylmethyl group, a benzoylmethyl group, an N,N-dimethylaminomethyl group, a methanesulfenylmethyl group, a methanesulfonylmethyl group, a phenylmethyl group, a phenethyl group, a phenoxymethyl group and a phenylthiomethyl group.

The $C_{2-6}$ alkenyl group which may be substituted, includes, for example, a vinyl group, a propenyl group, a 3,3,3-trifluoromethylpropenyl group, a butenyl group, a 2,2-dimethylvinyl group, a 2,2-dichlorovinyl group, a 2,2-difluorovinyl group, a 2,2-dicyanovinyl group, a 2,2-ditrifluoromethylvinyl group, a 2,2-dimethoxyvinyl group, a 2,2-dimethylthiovinyl group, a 2-methoxycarbonylvinyl group and a 2-phenylvinyl group.

The $C_{2-6}$ alkynyl group which may be substituted, includes, for example, an ethynyl group, a propynyl group, a phenylethynyl group and a trifluoromethylethynyl group.

The phenyl group which may be substituted, includes, for example, a hydroxyphenyl group, a toluyl group, a chlorophenyl group, a dimethylphenyl group, a trichlorophenyl group, a dimethoxyphenyl group, a pentafluorophenyl group, a methoxycarbonylphenyl group, a cyanophenyl group, a phenoxyphenyl group and a phenylthiophenyl group.

With respect to $R^7$ in the above formulas, the $C_{1-6}$ alkyl group which may be substituted, includes, for example, a methyl group, an ethyl group, a propyl group, a butyl group, an amyl group, a hexyl group, a trifluoroethyl group, a cyanomethyl group, a cyanoethyl group, a nitromethyl group, a nitroethyl group, a methoxycarbonylmethyl group, a methoxycarbonylethyl group, an ethoxycarbonylmethyl group, an ethoxycarbonylethyl group, a hydroxycarbonylmethyl group, a hydroxymethyl group, a hydroxyethyl group, a formylmethyl group, a methoxymethyl group, a methoxyethyl group, an ethoxymethyl group, an ethoxyethyl group, a methylthiomethyl group, a methylthioethyl group, an ethylthiomethyl group, an ethylthioethyl group, an acetylmethyl group, an acethylethyl group, a benzoylmethyl group, a benzoylethyl group, an N,N-dimethylaminomethyl group, a methanesulfenylmethyl group, a methanesulfonylmethyl group, a phenylmethyl group, a phenethyl group, a phenoxymethyl group, a phenoxyethyl group, a phenylthiomethyl group and a phenylthioethyl group.

The $C_{2-6}$ alkenyl group which may be substituted, includes, for example, a propenyl group, a 4,4,4-trifluoromethyl-2-butenyl group, a 3,3-dimethyl-2-propenyl group, a 3,3-dichloro-2-propenyl group, a 3,3-difluoro-2-propenyl group, a 3,3-dicyano-2-propenyl group, a 3,3-ditrifluoromethyl-2-propenyl group, a 3,3-dimethoxy-2-propenyl group, a 3,3-dimethylthio-2-propenyl group, a 3-methoxycarbonyl-2-propenyl group and a 3-phenyl-2-propenyl group.

The C$_{2-6}$ alkynyl group which may be substituted, includes, for example, a 2-propynyl group, a 3-phenyl-2-propynyl group, a 3-methoxycarbonyl-2-propynyl group, a 2-butynyl group, a 3-butynyl group and a 4,4,4-trifluoro-2-butynyl group.

The phenyl group which may be substituted, includes, for example, a hydroxyphenyl group, a tolyl group, a chlorophenyl group, a dimethylphenyl group, a trichlorophenyl group, a dimethoxyphenyl group, a pentafluorophenyl group, a methoxycarbonylphenyl group, a cyanophenyl group, a phenoxyphenyl group and a phenylthiophenyl group.

The above substituents are merely exemplary, and the present invention is by no means restricted to such specific examples.

Alkylating agents of the formula (II) may be used alone or in combination as a mixture of two or more of them.

The alkylating agent of the formula (II) is used usually in an amount of from 1.0 to 100 mol times, preferably from 1.0 to 10 mol times, relative to the heterocyclic secondary amine of the formula (I), although the reaction may proceed in an amount less than the stoichiometric amount relative to the heterocyclic secondary amine of the formula (I).

The catalyst of Group VIII of the Periodic Table includes an iron catalyst, a cobalt catalyst, a nickel catalyst, a ruthenium catalyst, a rhodium catalyst, a palladium catalyst, an osmium catalyst, an iridium catalyst and a platinum catalyst. Preferred is an iron catalyst, a cobalt catalyst, a ruthenium catalyst, a rhodium catalyst or a palladium catalyst. Particularly preferred is a ruthenium catalyst, a rhodium catalyst, and an iridium catalyst.

These catalysts may be used alone or in combination.

The iron catalyst includes, for example, iron pentacarbonyl and triiron dodecacarbonyl.

The cobalt catalyst may be dicobalt octacarbonyl.

The ruthenium catalyst includes, for example, triruthenium dodecacarbonyl, dichlorotris(triphenylphosphine)ruthenium, dichlorotris(tri-n-butylphosphine)ruthenium, dichlorotris(tri-i-butylphosphine)ruthenium, dichlorotris(tri-sec-butylphosphine)ruthenium, dichlorotris(tri-n-propylphosphine)ruthenium, dichlorotris(tri-i-propylphosphine)ruthenium, dichlorotris(triethylphosphine)ruthenium, dichlorotris(trimethylphosphine)ruthenium, dichlorotris(tritolylphosphene)ruthenium, dichlorotris(triphenylphosphite)ruthenium, dichlorotris(tri-n-butylphosphite)ruthenium, dichlorotris(tri-i-butylphosphite)ruthenium, dichlorotris(tri-sec-butylphosphite)ruthenium, dichlorotris(tri-n-propylphosphite)ruthenium, dichlorotris(tri-i-propylphosphite)ruthenium, dichlorotris(triethylphosphite)ruthenium, dichlorotris(trimethylphosphite)ruthenium, dichlorotris(tritolylphosphite)ruthenium, ruthenium trichloride, dicarbonyltris(triphenylphosphine)ruthenium, dicarbonyltris(tri-n-butylphosphine)ruthenium, dicarbonyltris(tri-i-butylphosphine)ruthenium, dicarbonyltris(tri-sec-butylphosphine)ruthenium, dicarbonyltris(tri-n-propylphosphine)ruthenium, dicarbonyltris(tri-i-propylphosphine)ruthenium, dicarbonyltris(triethyphosphine)ruthenium, dicarbonyltris(trimethylphosphine)ruthenium, dicarbonyltris(tritolylphosphine)ruthenium, dicarbonyltris(triphenylphosphine)ruthenium, dicarbonyltris(tri-n-butylphosphite)ruthenium, dicarbonyltris(tri-i-butylphosphite)ruthenium, dicarbonyltris(tri-sec-butylphosphite)ruthenium, dicarbonyltris(tri-n-propylphosphite)ruthenium, dicarbonyltris(tri-i-propylphosphite)ruthenium, dicarbonyltris(triethylphosphite)ruthenium, dicarbonyltris(trimethylphosphiste)ruthenium, dicarbonyltris(tritolylphosphite)ruthenium, carbonylchlorohydridotris(triphenylphosphine)ruthenium, carbonylchlorohydridotris(tri-n-butylphosphine)ruthenium, carbonylchlorohydridotris(tri-i-butylphosphine)ruthenium, carbonylchlorohydridotris(tri-sec-butylphosphine)ruthenium, carbonylchlorohydridotris(tri-n-propylphosphine)ruthenium, carbonylchlorohydridotris(tri-i-propylphosphine)ruthenium, carbonylchlorohydridotris(triethylphosphine)ruthenium, carbonylchlorohydridotris(trimethylphosphine)ruthenium, carbonylchlorohydridotris(tritolylphosphine)ruthenium, carbonylchlorohydridotris(triphenylphosphite)ruthenium, carbonylchlroohydridotris(tri-n-butylphosphite)ruthenium, carbonylchlorohydridotris(tri-i-butylphosphite)ruthenium, carbonylchlorohydridotris(tri-sec-butylphosphite)ruthenium, carbonylchlorodydridotris(tri-n-propylphosphite)ruthenium, carbonylchlorohydridotris(tri-i-propylphosphite)ruthenium, carbonylchlorohydridotris(triethylphosphite)ruthenium, carbonylchlorohydridotris(trimethylphosphite)ruthenium, carbonylchlorohydridotris(tritolylphosphite)ruthenium, carbonyldihydridotris(triphenylphosphine)ruthenium, carbonyldihydridotris(tri-n-butylphosphine)ruthenium, carbonyldihydridotris(tri-i-butylphosphine)ruthenium, carbonyldihydridotris(tri-sec-butylphosphine)ruthenium, carbonyldihydridotris(tri-n-propylphosphine)ruthenium, carbonyldihydridotris(tri-i-propylphosphine)ruthenium, carbonyldihydridotris(triethylphosphine)ruthenium, carbonyldihydridotris(trimethylphosphine)ruthenium, carbonyldihydridotris(tritolylphosphine)ruthenium, carbonyldihydridotris(triphenylphosphite)ruthenium, carbonyldihydridotris(tri-n-butylphosphite)ruthenium, carbonyldihydridotris(tri-i-butylphosphite)ruthenium, carbonyldihydridotris(tri-n-propylphosphite)ruthenium, carbonyldihydridotris(tri-i-propylphosphite)ruthenium, carbonyldihydridotris(triethylphosphite)ruthenium, carbonyldihydridotris(trimethylphosphite)ruthenium, carbonyldihydridotris(tritolylphosphite)ruthenium, tetracarbonyl(triphenylphosphin)ruthenium, tetracarbonyl(tri-n-butylphosphine)ruthenium, tetracarbonyl(tri-i-butylphosphine)ruthenium, tetracarbonyl(tri-sec-butylphosphin)ruthenium, tetracarbonyl(tri-n-propylphosphine)ruthenium, tetracarbonyl(tri-i-propylophosphine)ruthenium, tetracarbonyl(triethylphosphine)ruthenium, tetracarbonyl(trimethylphosphine)ruthenium, tetracarbonyl(tritolylphosphine)ruthenium, tetracarbonyl(triphenylphosphite)ruthanium, tetracarbonyl(tri-n-butylphosphite)ruthenium, tetracarbonyl(tri-i-butylphosphite)ruthenium, tetracarbonyl(tri-sec-butylphosphite)ruthenium, tetracarbonyl(tri-n-propylphosphite)ruthenium, tetracarbonyl(tri-i-propylphosphite)ruthenium, tetracarbonyl(triethylphosphite)ruthenium, tetracarbonyl(trimethylphosphite)ruthenium, tetracarbonyl(tritolylphosphite)ruthenium, dihydridotetrakis(triphenylphosphine),ruthenium, dihydridotetrakis(tri-n-butylphosphine)ruthenium, dihydridotetrakis(tri-i-butylphosphine)ruthenium, dihydridotetrakis(tri-sec-butylphosphine)ruthenium, dihydridotetrakis(tri-n-propylphosphine)ruthenium, dihydridotetrakis(tri-i-propylophosphine)ruthenium, dihydridotetrakis(triethylphosphine)ruthenium, dihydridotetrakis(trimethylphosphine)ruthenium, dihydridotetrakis(tritolylphosphine)ruthenium, dihydridotetrakis(triphenylphosphite)ruthenium, dihydridotetrakis(tri-n-butylphosphite)ruthenium, dihydridotetrakis(tri-i-butylphosphite)ruthenium, dihydridotetrakis(tri-sec-butylphosphite)ruthenium, dihydridotetrakis(tri-n-propylphosphite)ruthenium, dihydridotetrakis(tri-i-propylphosphite)ruthenium, dihydridotetrakis(triethylphosphite)ruthenium, dihydridotetrakis(trimethylphosphite)ruthenium, dihydridotetrakis(tritolylphosphite)ruthenium, chlorotris(triphenylphosphine)ruthenium, chlorotris(tri-n-butylphosphine)ruthenium, chlorotris(tri-i-butylphosphine)ruthenium, chlorotris(tri-sec-butylphosphine)ruthenium, chlorotris(tri-n-propylphosphine)ruthenium, chlorotris(tri-i-propylophosphine)ruthenium, chlorotris(triethylphosphine)ruthenium, chlorotris(trimethylphosphine)ruthenium, chlorotris(tritolylphosphine)ruthenium, chlorotris(triphenylphosphite)ruthenium, chlorotris(tri-n-butylphosphite)ruthenium, chlorotris(tri-i-butylphosphite)ruthenium, chlorotris(tri-sec-butylphosphite)ruthenium, chlorotris(tri-n-propylphosphite)ruthenium, chlorotris(tri-i-propylphosphite)ruthenium, chlorotris(triethylphosphite)ruthenium, chlorotris(trimethylphosphite)ruthenium, chlorotris(tritolylphosphite)ruthenium, tetrahydridododecacarbonyl tetraruthenium, diacetocarbonylbis(triphenylphosphine)ruthenium, diacetocarbonylbis(triphenylphosphite)ruthenium, diacetocarbonylbis(tri-n-butylphosphine)ruthienum, diacetocarbonylbis(tri-n-butylphosphite)ruthenium, diacetocarbonylbis(tri-i-propylphosphine)ruthenium, diacetocarbonylbis(tri-i-propylphosphite)ruthenium, tetracarbonylbis(cyclopentadienyl)diruthenium, chlorocarbonyl(cyclopentadienyl)ruthenium, tricarbonyl(cyclooocatetraene)ruthenium, tricarbonyl(1,5-cyclooctadiene)ruthenium, tricarbonylbis(triphenylphosphine)ruthenium, (cyclooocatriene)(cyclooctadiene)ruthenium and ruthenium trichloride.

The rhodium catalyst includes, for example, hexadecacarbonyl hexarhodium, tetrarhodium dodecacarbonyl, dichlorotetracarbonyl rhodium, hydridotetracarbonyl rhodium, hydridocarbonyltris(triphenylphosphine)rhodium, chlorotris(triphenylphosphine)rhodium, chlorotris(tri-n-butylphosphine)rhodium, chlorotris(tri-i-propylphosphine)rhodium, chlorotris(tri-n-propylphosphine)rhodium, chlorotris(triethylphosphine)rhodium, chlorotris(trimethylphosphine)rhodium, chlorotris(tri-o-tolylphosphine)rhodium, chlorotris(triphenylphosphite)rhodium, chlorotris(tri-n-butylphosphite)rhodium, chlorotris(tri-i-propylphosphite)rhodium, chlorotris(tri-n-propylphosphite)rhodium, chlorotris(triethylphosphite)rhodium, chlorotris(trimethylphosphite)rhodium, chlorotris(tri-o-tolylphosphite)rhodium and rhodium tetrachloride.

The palladium catalyst includes, for example, dichlorobis(triphenylphosphine)palladium, dichlorobis(trimethylphosphine)palladium, dichlorobis(tributylphosphine)palladium, bis(tricyclohexylphosphine)palladium, tetrakis(triethylphosphite)palladium, bis(cyclooocta-1,5-diene)palladium, tetrakis(triphenylphosphine)palladium, dicarbonylbis(triphenylphosphine)palladium, carbonyltris(triphenylphosphine)palladium, dichlorobis(benzonitrile)palladium, dichloro(1,5-cyclooocadiene)palladium, palladium chloride and palladium acetate.

The platinum catalyst includes, for example, dichlorobis(triphenylphosphine)platinum, dichlorobis(trimethylphosphine)platinum, dichlorobis(tributylphosphine)platinum, tetrakis(triphenylphosphine)platinum, tetrakis(triphenylphosphite)platinum, tris(triphenylphosphine)platinum, dicarbonylbis(triphenylphosphine)platinum, carbonyltris(triphenylphosphine)platinum, dichloroplatinum cis-bis(benzonitrile), bis(1,5-cyclooctadiene)platinum and platinum chloride.

The nickel catalyst includes, for example, dichlorobis(triphenylphosphine)nickel and nickel tetrakis(triphenylphosphine).

The iridium catalyst includes, for example, trichlorotris(triphenylphosphine)iridium, trichlorotris(tri-n-butylphosphine)iridium, trichlorotris(tri-i-butylphosphine)iridium, trichlorotris(tri-n-propylphosphine)iridium, trichlorotris(tri-i-propylphosphine)iridium, trichlorotris(triethylphosphine)iridium, trichlorotris(trimethylphosphine)iridium, trichlorotris(tri-o-tolylphosphine)iridium, trichlorotris(triphenylphosphite)iridium, trichlorotris(tri-n-butylphosphite)iridium, trichlorotris(tri-i-butylphosphite)iridium, trichlorotris(tri-n-propylphosphite)iridium, trichlorotris(tri-i-propylphosphite)iridium, trichlorotris(triethylphosphite)iridium, trichlorotris(trimethylphosphite)iridium, trichlorotris(tri-o-tolylphosphite)iridium, and iridium tetrachloride.

These catalysts of Group VIII of the Periodic Table are exemplary, and the present invention is by no means restricted to such specific examples.

The catalyst of Group VIII of the Periodic Table is used usually in an amount of from 0.01 to 20 mol %, preferably from 0.1 to 10 mol %, relative to the heterocyclic secondary amine of the formula (I). Further, a ligand or a reaction acceleration agent may be added to the reaction system, as the case requires, to carry out the reaction in a short period of time and in good yield.

The ligand includes, for example, a phosphorus compound, an arsenic compound, an antimony compound, a diene compound and a diketone compound. Particularly preferred is a phosphine or a phosphite. The phosphine includes, for example, an alkylphosphine such as triethylphosphine, tri-n-propylphosphine, tri-i-propylphosphine or tri-n-butylphosphine, and a triarylphosphine such as a triphenylphosphine.

The phosphite includes, for example, an alkyl phosphite such as triethyl phosphite, tri-n-propyl phosphite, tri-i-propyl phosphite or tri-n-butyl phosphite, and a triaryl phosphite such as triphenyl phosphite.

The ligand is used in an amount of from 0.01 to 500 mol %, preferably from 3 to 300 mol %, relative to the catalyst of Group VIII in the Periodic Table.

The reaction accelerator includes, for example, an organic or inorganic salt such as potassium chloride, potassium bromide, potassium iodide, sodium chloride, sodium bromide, sodium iodide, ammonium chloride, ammonium bromide, ammonium iodide, ammonium tetra-n-butyl bromide, phosphinium tetra-n-butyl bromide, ammonium benzyltriethyl chloride or ammonium benzyl triethyl bromide, an organic or inorganic acid such as formic acid, acetic acid, propionic acid, carbonic acid, carbon dioxide, hydrogen chloride, hydrogen bromide or hydrogen iodide, and an organic or inorganic base such triethylamine, dimethylaniline, pyridine, sodium hydroxide, potassium hydroxide, sodium hydride and potassium hydride.

Such a reaction accelerator is used in an amount of from 0.1 to 1,000 mol %, preferably from 1 to 200 mol %, to the catalyst metal. The above ligands and reaction accelerators are exemplary, and the present invention is by no means restricted to such specific examples.

The reaction may proceed without any solvent, but a solvent may be employed as the case requires.

The solvent may be an ether solvent such as diethyl ether, tetrahydrofuran, 1,4-dioxane, ethylene glycol diethyl ether, diethylene glycol diethyl ether or anisol, an aromatic solvent such as benzene, toluene or xylene, a halogenated aromatic solvent such as chlorobenzene, dimethylformamide, dimethylacetoamide, N-methylpyrrolidone, dimethylimidazolidinone or acetonitrile.

With respect to the pressure for the reaction, it is usually possible to employ a pressure of from 1 to 200 kg/cm$^2$ in an inert atmosphere such as nitrogen, argon or carbon dioxide. However, in view of the boiling points of the heterocyclic secondary amine of the formula (I) and the solvent, the reaction time and the reactivity, a pressure of from 1 to 150 kg/cm$^2$ is preferred.

The reaction temperature is usually from 15° to 300° C., preferably from 50° to 250° C.

The reaction time is selected depending upon e.g. the heterocyclic secondary amine of the formula (I) and the activity of the catalyst of Group VIII of the Periodic Table. It is usually from 0.5 to 100 hours, preferably from 1 to 30 hours.

With respect to the treatment after completion of the reaction, after removal of the solvent by e.g. distillation, as the case requires, the heterocyclic tertiary amine of the formula (III) can be isolated in a free form or in the form of a mineral acid salt by such a means as distillation under reduced pressure, recrystallization or chromatography purification. In some cases, it is possible to isolate the product in the form of an alkali metal salt, an alkaline earth metal salt or an ammonium salt.

According to the process of the present invention, the heterocyclic tertiary amine of the formula (III) can be obtained from a heterocyclic secondary amine of the formula (I) under a mild condition in good yield.

Especially when the alkylating agent of the formula (II) is an alcohol derivative, the reaction can be conducted under a neutral condition, whereby a relatively unstable heterocyclic secondary amine of the formula (I) can be employed.

For this reaction, a relatively inexpensive alkylating agent of the formula (II) can be employed, and there will be no substantial formation of by-products such as salts, whereby no substantial purification process is required. Thus, the process of the present invention is suitable as an industrial process.

Now, the present invention will be described in further detail with reference to Examples. However, it should be understood that the present invention is by no means restricted to such specific Examples.

EXAMPLE 1

Into a stainless steel autoclave having an internal capacity of 50 ml, 0.29 g (3.0 mmol) of 3,5-dimethylpyrazole, 0.39 g (12 mmol) of methanol, 13.6 mg (0.06 mmol) of ruthenium trichloride hydrate, 45 mg (0.18 mmol) of triethyl phosphite and 10 ml of dioxane were charged and reacted at 200° C. for 15 hours under a nitrogen pressure of 100 kg/cm$^2$.

The reaction solution was analyzed by gas chromatography, whereby the conversion of 3,5-dimethylpyrazole was 97.6%, and the yield of 1,3,5-trimethylpyrazole was 93.7%.

EXAMPLES 2 to 4

The reaction and operation were conducted in the same manner as in Example 1 except that the type of the catalyst was changed. The results are shown in Table 1.

TABLE 1

| Example No. | Catalyst | Conversion (%) | Yield (%) |
|---|---|---|---|
| 2 | RuCl$_3$ | 49.0 | 13.0 |
| 3 | RuHCl(CO)(PPh$_3$)$_3$ | 14.0 | 12.2 |
| 4 | RuH$_2$(CO)(PPh$_3$)$_3$ | 6.8 | 4.3 |

EXAMPLE 5

The reaction and operation were conducted in the same manner as in Example 1 except that 3,5-dimethylpyrazole was changed to 0.25 g (3.0 mmol) of 4-methylpyrazole.

The conversion of 4-methylpyrazole was 92.1%, and the yield of 1,4-dimethylpyrazole was 85.2%.

EXAMPLES 6 TO 10

The reaction and operation were conducted in the same manner as in Example 5 except that the types of the catalyst, the ligand and the alkylating agent of the formula (II) and the nitrogen pressure were changed. The results are shown in Table 2.

TABLE 2

| Example No. | Catalyst | Ligand | Alkylating agent | Pressure (kg/cm$^2$) | Conversion (%) | Yield (%) |
|---|---|---|---|---|---|---|
| 6 | RuCl$_3$ | (n-BuO)$_3$P | MeOH | 8.0 | 41.2 | 25.2 |
| 7 | RuCl$_3$ | (PhO)$_3$P | MeOH | 8.0 | 74.0 | 15.8 |
| 8 | RuCl$_2$(PPh$_3$)P | — | MeOH | 8.0 | 23.2 | 6.8 |
| 9 | RuCl$_3$ | (n-BuO)$_3$P | EtOH | 8.0 | 51.5 | 16.4 |
| 10 | RuCl$_2$(PPh$_3$)P | — | MeNH$_2$ | 100.0 | 11.4 | 3.4 |

In the Table, Me represents a methyl group, Et represents an ethyl group, Bu represents a butyl group and Ph represents a phenyl group.

EXAMPLES 11 to 17

The reaction and operation were conducted in the same manner as in Example 1 except that the type of the heterocyclic secondary amine of the formula (I) was changed. The results are shown in Table 3. Except for Examples 11 and 12 the corresponding N-methylated products were obtained. Example 16 demonstrates that 1,2,4-triazole also undergoes N-alkylation as described herein.

TABLE 3

| Example No. | Heterocyclic secondary amine | Conversion (%) | Yield (%) |
|---|---|---|---|
| 11 | 3-Methylpyrazole | 54.9 | 48.9[1)] |
| 12 | 3-Ethoxycarbonyl-5-methylpyrazole | 84.2 | 33.9[2)] |
| 13 | Imidazole | 33.8 | 18.6 |
| 14 | 2-Methylimidazole | 100 | 87.6 |
| 15 | Benzimidazole | 100 | 91.9 |
| 16 | 1,2,4-Triazole | 57.2 | 47.7 |

TABLE 3-continued

| Example No. | Heterocyclic secondary amine | Conversion (%) | Yield (%) |
|---|---|---|---|
| 17 | Imidazole | 100 | 98.1 |

[1]A mixture of 1,3-dimethylpyrazole:1,5-dimethylpyrazole = 46:54 was obtained.
[2]A mixture of 1,3-dimethyl product:1,5-dimethyl product = 86:14 was obtained.

EXAMPLE 18

Into a stainless steel autoclave having an internal capacity of 40 ml, 0.48 g (5.0 mmol) of 3,5-dimethylpyrazole, 0.64 g (20 mmol) of methanol, 29.9 mg (2 mol %) of iridium trichloride, 125 mg (10 mol %) of tributyl phosphite and 10 ml of 1,4-dioxane were charged and reacted at 200° C. for 20 hours under a nitrogen pressure of 100 kg/cm$^2$, whereby the yield of 1,3,5-trimethylpyrazole was 90.7%.

EXAMPLE 19

The reaction and operation were conducted in the same manner as in Example 18 except that iridium trichloride was changed to 20.9 mg (2 mol %) of rhodium trichloride, whereby the yield of 1,3,5-trimethylpyrazole was 90.4%.

EXAMPLE 20

Into a stainless steel autoclave having an internal capacity of 40 ml, 0.48 g (5.0 mmol) of 3,5-dimethylpyrazole, 0.64 g (20 mmol) of methanol, 26.0 mg (2 mol %) of ruthenium trichloride, 125 mg (10 mol %) of tributyl phosphite, 35.5 mg (0.25 mmol) of methyl iodide and 10 ml of 1,4-dioxane were charged and reacted at 150° C. for 20 hours under an argon pressure of 20 kg/cm$^2$, whereby the yield of 1,3,5-trimethylpyrazole was 99.4%.

EXAMPLE 21

The reaction and operation were conducted in the same manner as in Example 20 except that ruthenium trichloride was changed to 20.9 mg (2 mol %) of rhodium trichloride, whereby the yield of 1,3,5-trimethylpyrazole was 99.8%.

EXAMPLE 22

The reaction and operation were conducted in the same manner as in Example 20 except that methyl iodide was changed to 41.5 mg of potassium iodide, whereby the yield of 1,3,5-trimethylpyrazole was 32.8%.

EXAMPLE 23

The reaction and operation were conducted in the same manner as in Example 20 except that methyl iodide was changed to 50.3 mg of tetramethyl ammonium iodide, whereby the yield of 1,3,5-trimethylpyrazole was 99.7%.

EXAMPLE 24

The reaction and operation were conducted in the same manner as in Example 20 except that methanol was changed to 0.927 g of ethanol, methyl iodide was changed to 39.3 mg of ethyl iodide, and tributyl phosphite was changed to 83 mg of triethyl phosphite, whereby the yield of 1-ethyl-3,5-trimethylpyrazole was 92.8%.

EXAMPLE 25

The reaction and operation were conducted in the same manner as in Example 20 except that methanol was changed to 1.46 g of isopropanol, methyl iodide was changed to 42.5 mg of isopropyl iodide and tributyl phosphite was changed to 104 mg of triisopropyl phosphite, whereby the yield of 1-isopropyl-3,5-trimethylpyrazole was 43%.

EXAMPLES 27 TO 32

The reaction and operation were conducted in the same manner as in Example 1 except that the types of the ligand and the solvent were changed. The results are shown in Table 4.

TABLE 4

| Example No. | Ligand | Solvent | Yield (%) |
|---|---|---|---|
| 27 | (n-BuO)$_3$P | Benzene | 92.9 |
| 28 | (n-BuO)$_3$P | Acetonitrile | 96.5 |
| 29 | (n-BuO)$_3$P | N-methylpyrrolidone | 87.9 |
| 30 | (i-PrO)$_3$P | n-Hexane | 92.8 |
| 31 | (i-PrO)$_3$P | Water | 7.2 |
| 32 | (i-PrO)$_3$P | No solvent | 96.1 |

In the Table, i-Pr represents an isopropyl group, and Bu represents a butyl group.

EXAMPLES 33 TO 35

The reaction and operation were conducted in the same manner as in Example 20 except that no methyl iodide was added, and the type of the alkylating agent of the formula (II) was changed. The results are shown in Table 5.

TABLE 5

| Example No. | Alkylating agent | Yield (%) |
|---|---|---|
| 33 | Allyl alcohol | 31.4 |
| 34 | Ethoxydiethyl alcohol | 11.5 |
| 35 | n-Butanol | 26.1 |

In the Table, i-Pr represents an isopropyl group, and Bu represents a butyl group.

EXAMPLE 36

The reaction and operation were conducted in the same manner as in Example 18 except that iridium trichloride was changed to 26.0 g of ruthenium trichloride, the nitrogen pressure of 100 kg/cm$^2$ was changed to a carbon dioxide pressure of 50 kg/cm$^2$, whereby the yield of 1,3,5 trimethylpyrazole was 98.5%.

EXAMPLE 37

Into a stainless steel autoclave having an internal capacity of 40 ml, 0.41 g (5.0 mmol) of 4-methylpyrazole, 0.64 g (20 mmol) of methanol, 26.0 mg (2 mol %) of ruthenium trichloride, 125 mg (10 mol %) of tributyl phosphite, 35.5 mg (0.25 mmol) of methyl iodide and 10 ml of 1,4-dioxane were charged and reacted at 150° C. for 20 hours under an argon pressure of 20 kg/cm$^2$, whereby the yield of 1,4-dimethylpyrazole was 99.0%.

EXAMPLE 38

The reaction and operation were conducted in the same manner as in Example 37 except that ruthenium trichloride was changed to 20.9 mg (2 mol %) of rhodium trichloride, whereby the yield of 1,4-dimethylpyrazole was 99.5%.

EXAMPLE 39

The reaction and operation were conducted in the same manner as in Example 37 except that methyl iodide was changed to 41.5 mg of potassium iodide, whereby the yield of 1,4-dimethylpyrazole was 55.3 %.

EXAMPLE 40

The reaction and operation were conducted in the same manner as in Example 37 except that methyl iodide was changed to 50.3 mg of tetramethyl ammonium iodide, whereby the yield of 1,4-dimethylpyrazole was 99.7%.

We claim:

1. A process for producing an aromatic heterocyclic tertiary amine of the formula (III):

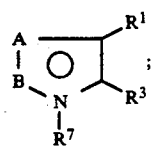

wherein A is a nitrogen atom or C-$R^5$, B is a nitrogen atom or C-$R^6$, and each of $R^1$, $R^3$, $R^5$ and $R^6$ which may be the same or different, is a hydrogen atom, an acyl group, a halogen atom, a cyano group, a nitro group, a carboxyl group, a formyl group, a trialkylsilyl group, a $C_{1-6}$ alkoxycarbonyl group which may be substituted (the substituent being a hydroxyl group, a halogen atom, a cyano group, a nitro group, a carboxyl group, a formyl group a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a phenyl group, a phenoxy group or a phenylthio group), a $C_{1-6}$ alkylcarbonyloxy group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a phenyl group, a phenoxy group or a phenylthio group), a $C_{1-6}$ alkoxy group which may be substituted (the substituent being a hydroxyl group, a halogen atom, a cyano group, a nitro group, a carboxyl group, a formyl group, a lower alkoxy group, a lower alkylthio group, a lower alkoxy carbonyl group, an acyl group, a benzoyl group, a di-lower alkylamino group, a lower alkylsulfenyl group, a lower alkylsulfonyl group, a phenyl group, a phenoxy group or a phenylthio group), a $C_{1-6}$ dialkylamino group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a phenyl group, a phenoxy group or a phenylthio group), a $C_{1-6}$ alkylthio group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a phenyl group, a phenoxy group or a phenylthio group), a $C_{1-6}$ alkylsulfenyl group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a phenyl group, a phenoxy group or a phenylthio group), a $C_{1-6}$ alkylsulfonyl group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a phenyl group, a phenoxy group or a phenylthio group), a $C_{1-6}$ alkylsulfonyloxy group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a phenyl group, a phenoxy group or a phenylthio group), a $C_{1-6}$ alkyl group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a phenyl group, a phenoxy group or a phenylthio group), a $C_{2-6}$ alkenyl group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a phenyl group, a phenoxy group or a phenylthio group), a $C_{2-6}$ alkynyl group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulphenyl group, a lower alkylsulphonyl group, a phenyl group, a phenoxy group or a phenylthio group), or a phenyl group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a phenyl group, a phenoxy group or a phenylthio group), provided that $R^1$, $R^3$ and may together form a aromatic ring, and $R^7$ is a $C_{1-6}$ alkyl group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a trialkylsilyl group, a phenyl group, a phenoxy group or a phenylthio group), a $C_{2-6}$ alkenyl group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a trialkylsilyl group, a phenyl group, a phenoxy group or a phenylthio group), a $C_{2-6}$ alkynyl group which may be substituted (the substituent being a hydroxyl group, a halogen atom, a cyano group, an nitro group, a carboxyl group, a formyl group, a lower alkoxy group, a lower alkylthio group, a lower alkoxycarbonyl group, an acyl group, a benzoyl group, a di-lower alkylamino group, a ruthenium trialkylsilyl group, a phenyl group, a phenoxy group or a phenylthio group), or a phenyl group which may be substituted (the substituent being a hydroxyl group, a halogen atom, a cyano group, a nitro group, a carboxyl group, a formyl group, a lower alkoxy group, a lower alkylthio group, a lower alkoxy carbonyl group, an acyl group, a benzoyl group, a di-lower alkylamino group, a lower alkylsulfenyl group, a lower alkylsulfonyl group, a trialkylsilyl group, a phenyl group, a phenoxy group or a phenylthio group), which process comprises reacting a heterocyclic secondary amine of the formula (I):

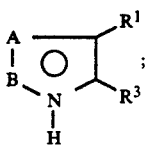

(I)

wherein A, B, $R^1$, $R^3$ and are as defined above, with an alkylating agent of the formula (II):

(II)

wherein $R^7$ is as defined above, and X is a hydroxyl group, a halogen atom, a $OSO_3R^7$ group, a $OSO_2R^7$ group, a $OCO_2R^7$ group, a $OCOR^7$ group, a $OP(O)(OR^7)$ group, a $OP(O)O(R^7)_2$ group or an amino group, in the presence of a catalyst of Group VIII of the Periodic Table.

2. The process for producing an aromatic heterocyclic tertiary amine according to claim 1, wherein the ruthenium catalyst is selected from dichlorotris(triphenylphosphine)ruthenium, dichlorotris(tri-n-butylphosphite)ruthenium, dichlorotri(tri-n-propylphosphite)ruthenium, dichlorotris(tri-i-propylphosphite)ruthenium, dichlorotris(triethylphosphite)ruthenium, dichlorotris(tributylphosphine)ruthenium, dichlorotris(tritolylphosphine)ruthenium, ruthenium trichloride, carbonylchlorohydridotris(triphenylphosphine)ruthenium, carbonylchlorohydridotris(tri-n-butylphosphine)ruthenium, carbonylchlorohydridotris(triphenylphosphite)ruthenium, carbonylchlorohydridotris(tri-n-butylphosphite)ruthenium, carbonylchlorohydridotris(tri-n-propylphosphite)ruthenium, carbonylchlorohydridotris(tri-i-propylphosphite)ruthenium, carbonylchlorohydridotris(triethylphosphite)ruthenium, carbonyldihydridotris(triphenylphosphine)ruthenium, carbonyldihydridotris(tri-n-butylphosphine)ruthenium, carbonyldihydridotris(triphenylphosphite)ruthenium, carbonyldihydridotris(tri-n-butylphosphite)ruthenium, carbonyldihydridotris(tri-n-propylphosphite)ruthenium, carbonyldihydridotris(tri-i-propylphosphite)ruthenium, carbonyldihydridotris(triethylphosphite)ruthenium, dihydridotetrakis(triphenylphosphine)ruthenium, dihydridotetrakis(tri-n-butylphosphine)ruthenium, dihydridotetrakis(tri-n-butylphosphite)ruthenium, dihydridotetrakis(tri-n-propylphosphite)ruthenium, dihydridotetrakis(tri-i-propylphosphite)ruthenium and dihydridotetrakis(triethylphosphite)ruthenium.

3. The process for producing an aromatic heterocyclic tertiary amine according to claim 1, wherein a ligand selected from a trialkylphosphine, a triarylphosphine, a trialkyl phosphite and a triaryl phosphite, is added.

4. The process for producing an aromatic heterocyclic tertiary amine according to claim 1 wherein X is a hydroxyl group.

5. The process for producing an aromatic heterocyclic tertiary amine according to claim 4, wherein A is C-$R^5$, B is a nitrogen atom, $R^3$, $R^5$, and $R^7$ are methyl, and $R^1$ is hydrogen.

6. The process for producing an aromatic heterocyclic tertiary amine according to claim 4, wherein A is C-$R^5$, B is a nitrogen atom, $R^1$ and $R^7$ are methyl, and $R^3$ and $R^5$ are hydrogen.

7. A process for producing N-substituted products of 1,2,4-triazole comprising reacting 1,2,4-triazole with an alkylating agent of the formula $R^7$-X wherein $R^7$ is a $C_{1-6}$ alkyl group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a trialkylsilyl group, a phenyl group, a phenoxy group or a phenylthio group), a $C_{2-6}$ alkenyl group which may be substituted (the substituent being a hydroxyl group, a halogen atom, a cyano group, a nitro group, a lower alkylthio group, a lower alkoxycarbonyl group, an acyl group, a benzoyl group, a di-lower alkylamino group, a lower alkylsulfenyl group, a lower alkylsulfonyl group, a trialkylsilyl group, a phenyl group, a phenoxy group or a phenylthio group), a $C_{2-6}$ alkynyl group which may be substituted (the substituent being a hydroxyl group, a halogen atom, a cyano group, a nitro group, a carboxyl group, a formyl group, a lower alkoxy group, a lower alkylthio group, a lower alkoxycarbonyl group, an acyl group, a benzoyl group, a di-lower alkylamino group, a lower alkylsulfenyl group, a lower alkylsulfonyl group, a trialkylsilyl group, a phenyl group, a phenoxy group or a phenylthio group), or a phenyl group which may be substituted (the substituent being a hydroxyl group, a halogen atom, a cyano group, a nitro group, carboxyl group, a formyl group, a lower alkoxy group, a lower alkylthio group, a lower alkoxy carbonyl group, an acyl group, a benzoyl group, a di-lower alkylamino group, a lower alkylsulfenyl group, a lower alkylsulfonyl group, a trialkylsilyl group, a phenyl group, a phenoxy group or a phenylthio group), and X is a hydroxyl group, a halogen atom, a $OSO_3R^7$ group, a $OSO_2R^7$ group, a $OCO_2R^7$ group, a $OCOR^7$ group, a $OP(O)(OR^7)$ group, a $OP(O)O(R^7)_2$ group or an amino group, in the presence of a ruthenium catalyst of.

8. The process for producing a heterocyclic tertiary amine according to claim 7, wherein X is a hydroxyl group.

* * * * *